(12) United States Patent
Hijnen et al.

(10) Patent No.: US 10,966,632 B2
(45) Date of Patent: Apr. 6, 2021

(54) METHOD AND DEVICE FOR DETERMINING THE HEALTH OF A SUBJECT

(71) Applicant: KONINKLIJKE PHILIPS N.V., Eindhoven (NL)

(72) Inventors: Nicole Maria Hijnen, Eindhoven (NL); Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 743 days.

(21) Appl. No.: 15/526,630

(22) PCT Filed: Nov. 10, 2015

(86) PCT No.: PCT/EP2015/076229
§ 371 (c)(1),
(2) Date: May 12, 2017

(87) PCT Pub. No.: WO2016/078972
PCT Pub. Date: May 26, 2016

(65) Prior Publication Data
US 2017/0319104 A1 Nov. 9, 2017

(30) Foreign Application Priority Data
Nov. 19, 2014 (EP) .................................... 14193872

(51) Int. Cl.
*A61B 5/08* (2006.01)
*A61B 5/091* (2006.01)
(Continued)

(52) U.S. Cl.
CPC ............ *A61B 5/082* (2013.01); *A61B 5/0878* (2013.01); *A61B 5/091* (2013.01); *A61B 5/4875* (2013.01);
(Continued)

(58) Field of Classification Search
CPC ......... A61B 5/082; A61B 5/087; A61B 5/091; A61B 5/4875; A61B 2562/029; A61M 16/00–161; A61M 2230/40–43
See application file for complete search history.

(56) References Cited

U.S. PATENT DOCUMENTS 3,026,868 A 3/1962 Weinberg
2004/0221844 A1 11/2004 Hunt et al.
(Continued)

FOREIGN PATENT DOCUMENTS

EP 0885623 A2 12/1998
EP 2436310 A1 4/2012

OTHER PUBLICATIONS

Bates, et al., "Tidal breath analysis for infant pulmonary function testing", European Respiratory Journal 2000; 16; pp. 1180-1192.
(Continued)

*Primary Examiner* — Daniel L Cerioni
*Assistant Examiner* — Raymond P Dulman

(57) ABSTRACT

According to an aspect there is provided a method of determining the health of a subject, the method comprising determining the absolute humidity and volume of air exhaled by the subject over time; and analysing the determined absolute humidity and volume of air exhaled by the subject to determine a characteristic of the air that was above the isothermic saturation boundary, ISB, of the subject.

14 Claims, 6 Drawing Sheets

(51) Int. Cl.
*A61B 5/00* (2006.01)
*A61M 16/16* (2006.01)
*A61B 5/087* (2006.01)
*A61M 16/00* (2006.01)

(52) U.S. Cl.
CPC ...... *A61M 16/0057* (2013.01); *A61M 16/161* (2014.02); *A61B 5/087* (2013.01); *A61B 2562/029* (2013.01); *A61M 2230/40* (2013.01)

(56) References Cited

U.S. PATENT DOCUMENTS

| | | | |
|---|---|---|---|
| 2007/0107728 A1 | 5/2007 | Ricciardelli et al. | |
| 2009/0112114 A1 | 4/2009 | Ayyagari et al. | |
| 2009/0223514 A1* | 9/2009 | Smith | A61M 16/1075 128/203.14 |
| 2009/0272656 A1* | 11/2009 | Varney | A61B 5/0836 205/785.5 |
| 2009/0301478 A1* | 12/2009 | Ohmura | A61M 16/1045 128/201.13 |
| 2014/0116433 A1* | 5/2014 | Ghalib | A61M 16/026 128/203.14 |
| 2014/0318535 A1* | 10/2014 | Bullock | A61M 16/16 128/202.15 |
| 2014/0336523 A1* | 11/2014 | Brix | A61B 5/0833 600/531 |
| 2015/0196251 A1* | 7/2015 | Outwater | A61B 5/4875 600/301 |
| 2015/0217079 A1* | 8/2015 | Mcauley | A61M 16/109 128/203.14 |

OTHER PUBLICATIONS

Van den Boer, et al., "A novel, simplified ex vivo method for measuring water exchange performance of Heat and Moisture Exchangers for tracheostomy application", Respiratory Care Paper in Press, Published Mar. 12, 2013 as DOI:10.4187/respcare.02369.
Niesters, et al., "Validation of a novel respiratory rate monitor based on exhaled humidity", British Journal of Anaesthesia, published Aug. 19, 2012, pp. 1-9.
Scheenstra, et al., "A New Heat and Moisture Exchanger for Laryngectomized Patients: Endotracheal Temperature and Humidity", Respiratory Care, May 2011, vol. 56, No. 5, pp. 604-611.
Scheenstra, et al., "Endotracheal temperature and humidity measurements in laryngectomized patients: intra- and inter-patient variability", Med. Biol. Eng. Comput (2009); 47; pp. 773-782.

* cited by examiner

US 10,966,632 B2

METHOD AND DEVICE FOR DETERMINING THE HEALTH OF A SUBJECT

This application is the U.S. National Phase application under 35 U.S.C. §371 of International Application No. PCT/EP2015/076229, filed on Nov. 10, 2015, which claims the benefit of European Application No. 14193872.0, filed Nov. 19, 2014. These applications are hereby incorporated by reference herein.

TECHNICAL FIELD OF THE INVENTION

The invention relates to a method and device for determining the health of a subject, and in particular relates to a method and device for determining the health of a subject based on characteristics of the air exhaled by the subject.

BACKGROUND TO THE INVENTION

Current exhaled breath analysis is directed towards measuring biomarkers (e.g. nitric oxide, cytokines, and $H_2O_2$) in the exhaled breath condensate (EBC). This type of analysis is gaining in popularity for the detection and analysis of multiple respiratory disorders, including airway inflammation. For these purposes, the absolute EBC volume (directly related to its humidity) is of interest only as a means of generating a sample size large enough for biomarker analysis, and defining biomarker dilution. There are several devices on the market (e.g. RTube and ECoScreen) designed to collect the exhaled breath condensate.

These devices are designed for sample collection and cool the exhaled breath down to induce condensation to allow subsequent analysis of biomarkers. They collect the entire exhaled breath volume of multiple breaths, typically during a fixed time interval or until a large enough condensate volume has been sampled.

The isothermic saturation boundary (ISB) in a subject is the point in the respiratory system of the subject where inhaled air reaches body temperature (around 37° C) and is completely saturated with water (around 44 grams/metre$^3$).

SUMMARY OF THE INVENTION

It has been found that the ISB of a subject can provide useful information on the health of the subject, particularly the hydration status of the subject (e.g. an indication of whether the subject is dehydrated), and therefore it is desirable to provide a method and device for determining the health of a subject that determines a characteristic of the air that was above the ISB of the subject from an analysis of exhaled breath.

According to a first aspect of the invention, there is provided a method of determining the health of a subject, the method comprising determining the absolute humidity and volume of air exhaled by the subject over time; and analysing the determined absolute humidity and volume of air exhaled by the subject to determine a characteristic of the air that was above the isothermic saturation boundary, ISB, of the subject.

In some embodiments the method further comprises the step of using the characteristic of the air that was above the ISB of the subject to estimate the hydration level of the subject.

In some embodiments the step of using the characteristic of the air that was above the ISB to estimate the hydration level of the subject comprises comparing the characteristic of the air that was above the ISB to a set of reference values.

In some embodiments the step of using the characteristic of the air that was above the ISB to estimate the hydration level comprises correcting the characteristic of the air that was above the ISB for the shape and/or size of the subject.

In some embodiments the step of correcting the characteristic of the air that was above the ISB for the shape and/or size of the subject comprises correcting the characteristic of the air that was above the ISB according to the weight, height or body mass index, BMI, of the subject.

In some embodiments the step of determining the absolute humidity and volume of air exhaled by the subject over time comprises measuring the absolute humidity using an absolute humidity sensor.

In alternative embodiments the step of determining the absolute humidity and volume of air exhaled by the subject over time comprises measuring the relative humidity and temperature of the air exhaled by the subject and using the measured relative humidity and temperature to determine the absolute humidity of the air exhaled by the subject over time.

In some embodiments the step of determining the absolute humidity and volume of air exhaled by the subject over time comprises measuring the flow rate as air is exhaled by the subject and determining the volume of air exhaled by the subject from the measured flow rate.

In alternative embodiments the step of determining the absolute humidity and volume of air exhaled by the subject over time comprises measuring the air pressure as air is exhaled by the subject and determining the volume of air exhaled by the subject from the measured air pressure.

In some embodiments the method further comprises the step of correcting the characteristic of the air that was above the ISB of the subject for the ambient conditions of the air inhaled by the subject. In some embodiments the ambient conditions comprise the absolute humidity of the air inhaled by the subject. In alternative embodiments, the ambient conditions comprise the relative humidity and temperature of the air inhaled by the subject.

In alternative embodiments the method further comprises the step of controlling the ambient conditions of the air inhaled by the subject.

In some embodiments the characteristic of the air that was above the ISB is the volume of air above the ISB in the subject. In these embodiments, the volume of air above the ISB in the subject can be determined as the volume of air exhaled by the subject from the start of an exhalation until the absolute humidity is at a predetermined amount of a maximum value. In some embodiments the predetermined amount is 100%. In other embodiments, the predetermined amount can be below 100%, for example 95%.

In some embodiments the characteristic of the air that was above the ISB in the subject is any one or more of (i) the volume of air above the ISB in the subject; (ii) the area under a plot of the absolute humidity against time; (iii) the area under part of a plot of the absolute humidity against time; (iv) the amplitude of the absolute humidity after a specific time interval from the start of the exhalation; and (v) the slope, gradient, rate of change or rising slope of the absolute humidity at a specific time or over part of the exhalation by the subject.

According to a second aspect of the invention, there is provided a computer program product comprising a computer readable medium having computer readable code embodied therein, the computer readable code being configured such that, on execution by a suitable computer, processor or control unit, the computer, processor or control unit is caused to perform any of the methods described above.

According to a third aspect of the invention, there is provided a device for determining the health of a subject, the device comprising a control unit configured to determine the absolute humidity and volume of air exhaled by the subject over time; and analyse the determined absolute humidity and volume of air exhaled by the subject to determine a characteristic of the air that was above the isothermic saturation boundary, ISB, of the subject.

In some embodiments the control unit is further configured to use the characteristic of the air that was above the ISB of the subject to estimate the hydration level of the subject.

In some embodiments the control unit is configured to use the characteristic of the air that was above the ISB to estimate the hydration level of the subject by comparing the characteristic of the air that was above the ISB to a set of reference values.

In some embodiments the control unit is configured to use the characteristic of the air that was above the ISB to estimate the hydration level by correcting the characteristic of the air that was above the ISB for the shape and/or size of the subject. In some embodiments the control unit is configured to correct the characteristic of the air that was above the ISB for the shape and/or size of the subject by correcting the characteristic of the air that was above the ISB according to the weight, height or body mass index, BMI, of the subject.

In some embodiments the device further comprises an absolute humidity sensor for measuring the absolute humidity of the air exhaled by the subject.

In alternative ebodiments the device further comprises a relative humidity sensor and a temperature sensor for measuring the relative humidity and temperature of the air exhaled by the subject respectively, and the control unit is configured to determine the absolute humidity of air exhaled by the subject over time from the measured relative humidity and temperature.

In some embodiments the device further comprises an air flow sensor for measuring the flow of air exhaled by the subject, and the control unit is configured to determine the volume of air exhaled by the subject from the measured flow rate.

In alternative embodiments the device further comprises an air pressure sensor for measuring the air pressure as air is exhaled by the subject, and the control unit is configured to determine the volume of air exhaled by the subject from the measured air pressure.

In some embodiments the control unit is further configured to correct the characteristic of the air that was above the ISB of the subject for the ambient conditions of the air inhaled by the subject. In some embodiments the ambient conditions comprise the absolute humidity of the air inhaled by the subject. In alternative embodiments the ambient conditions comprise the relative humidity and temperature of the air inhaled by the subject.

In alternative embodiments the device further comprises an apparatus for controlling the ambient conditions of the air inhaled by the subject.

In some embodiments the characteristic of the air that was above the ISB is the volume of air above the ISB in the subject. In these embodiments, the control unit can be configured to determine the volume of air above the ISB in the subject as the volume of air exhaled by the subject from the start of an exhalation until the absolute humidity is at a predetermined amount of a maximum value. In some embodiments the predetermined amount is 100%. In other embodiments, the predetermined amount can be below 100%, for example 95%.

In some embodiments the characteristic of the air that was above the ISB in the subject is any one or more of (i) the volume of air above the ISB in the subject; (ii) the area under a plot of the absolute humidity against time; (iii) the area under part of a plot of the absolute humidity against time; (iv) the amplitude of the absolute humidity after a specific time interval from the start of the exhalation; and (v) the slope, gradient, rate of change or rising slope of the absolute humidity at a specific time or over part of the exhalation by the subject.

In some embodiments, the device comprises a housing and a breathing tube through which the subject exhales. In some embodiments, the breathing tube and housing are configured so that the breathing tube can be removed from the housing and replaced.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
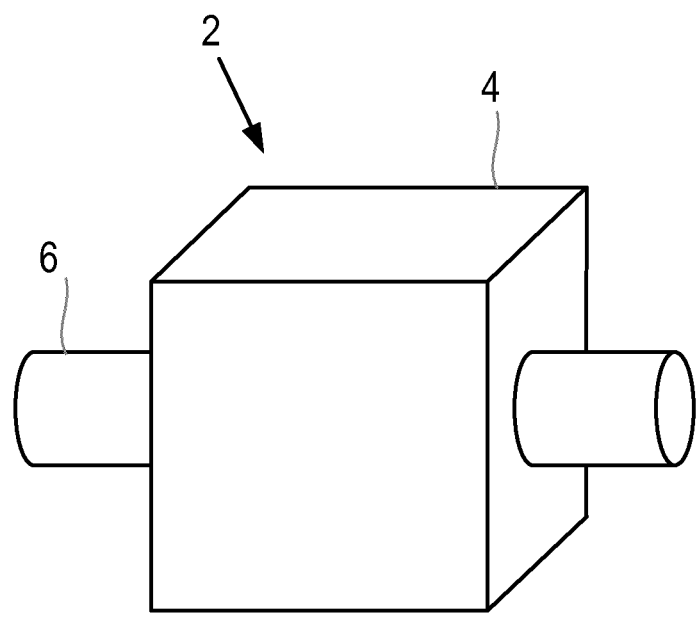
FIG. 1 is a diagram illustrating a device according to an embodiment of the
invention.

FIG. 1 is a diagram illustrating a device according to an embodiment of the invention. The device 2 is a small handheld device that comprises a housing 4 and a breathing tube 6 through which a subject is to inhale and exhale. One or more sensors are contained within the device 2 that measure properties of the air exhaled by the subject and that are analysed by the device 2 to determine a characteristic of the air that was above the isothermal saturation boundary (ISB) of the subject. The one or more sensors are not shown in FIG. 1, but they are generally arranged to measure the properties as air is exhaled through the breathing tube 6 by the subject. In some embodiments, the one or more sensors also measure the same or different properties of air as it is inhaled by the subject through the device 2. In this description, references to 'exhaled air' are to air that has been exhaled into the device 2 by the subject, and references to 'inhaled air' are to air that is being drawn into and through the device 2 by the subject inhaling through the breathing tube 6 (and not to air that is already within the body of the subject).

In FIG. 1 the breathing tube 6 is shaped so that it can be placed in or at the mouth of the subject, but in other embodiments, the breathing tube 6 can be shaped so that it can be placed in or at a nostril of the subject. It will be appreciated that the breathing tube 6 can comprise any suitable type of patient interface to enable it to be easily used by the subject, for example a mouthpiece, a nasal cannula, a nasal mask, a nasal oral mask, a full face mask, and a total face mask. The tube 6 can be thermally insulating or thermally isolating so that it prevents significant cooling of the exhaled air inside the tube 6.

Figure 2:
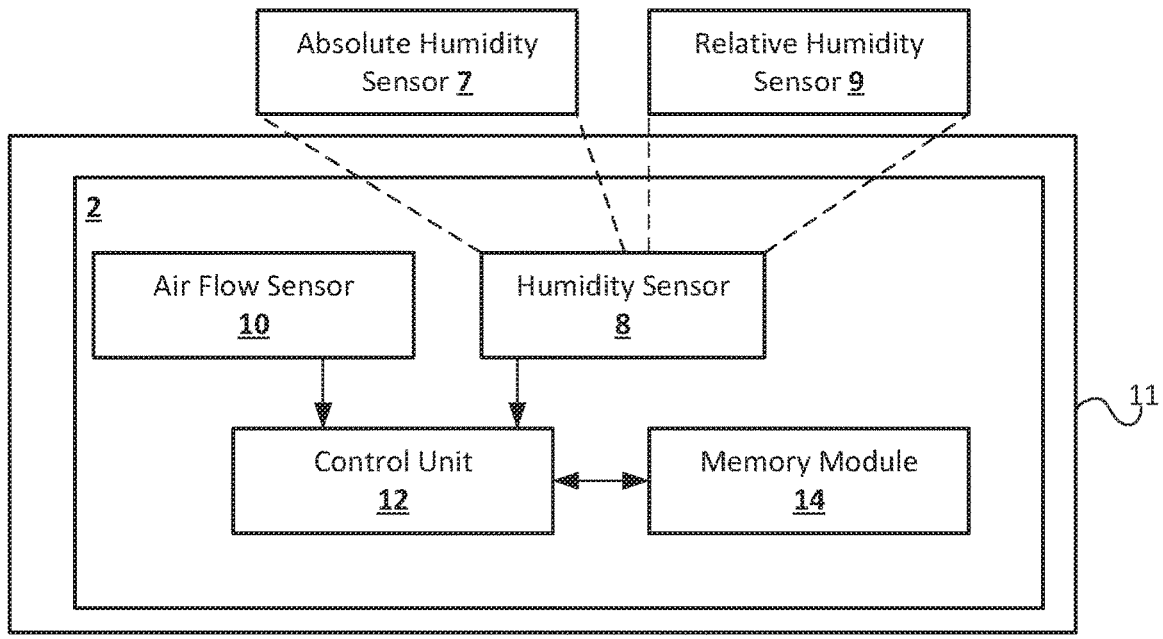
FIG. 2 is a block diagram of a device according to an embodiment of the
invention.

A block diagram of the device 2 according to an embodiment is shown in FIG. 2. In this embodiment, the device 2 comprises a humidity sensor 8 for measuring the humidity of the air being exhaled by the subject as it passes through the device 2 (and optionally also the humidity of the air that is being inhaled by the subject as it passes through the device 2) and an air flow sensor 10 for measuring the flow rate of the air passing through the device as the subject exhales and inhales. Signals from the humidity sensor 8 and air flow sensor 10 representing the humidity and air flow respectively are output to a control unit 12 that processes the signals to determine a characteristic of the air that was above the ISB of the subject.

The control unit 12 controls the operation of the device 2 according to the invention. The control unit 12 can comprise one or more processors, processing units, multi-core processors or processing modules. The device 2 further comprises a memory module 14 for storing computer readable program code that can be executed by the control unit 12 to perform the method according to the invention. The memory module 14 can also be used to store the sensor measurements before, during and after processing by the control unit 12 and any intermediate products of the processing.

In this illustrated embodiment of the invention, the device 2 comprises a single unit or device that is held by the subject and that collects and processes the sensor signals/measurements (in the control unit 12) to determine the characteristic of the air that was above the ISB of the subject. In alternative embodiments, the processing of the signals/measurements can be performed in a control unit that is remote from the device 2 (for example in a base unit or computer that can be located in the subject's home or in a healthcare environment, or a remote server located in the premises of a healthcare service provider), in which case the device 2 will comprise suitable transmitter, transceiver or communication circuitry (not shown) for transmitting the measurements wirelessly to a control unit in the remote unit. In either embodiment, the device 2 can be part of a monitoring system which comprises a display or other visual indicator (that can themselves be part of or separate from the device 2) that can be used to indicate the determined characteristic of the air that was above the ISB of the subject to the subject or a clinician/healthcare professional.

In practical implementations, the device 2 may comprise other or further components to those shown in FIG. 2 and described above, such as a user interface that allows the subject or clinician to activate and/or operate the device 2, and a power supply, such as a battery, for powering the device 2. The user interface may comprise one or more components that allow a user (e.g. the subject) to interact and control the device 2. As an example, the one or more user interface components could comprise a switch, a button or other control means for activating and deactivating the device 2. The user interface components can also or alternatively comprise a display or other visual indicator for providing information to the subject about the operation of the device 2, including displaying the determined characteristic of the air that was above the ISB.

In some embodiments of the invention, as described in more detail below, the humidity sensor 8 can be either a relative humidity sensor 9 or an absolute humidity sensor 7. Relative humidity is the ratio of partial pressure of water vapour in the mixture over the saturated vapour pressure at those conditions and is expressed as a percentage. For example, the relative humidity in human lungs is 100%, as for those conditions (temperature, NaCl counterpart in tissue) the air could not contain more water. Absolute humidity is independent of the conditions, and expressed as the mass of water vapour per unit volume of air and water vapour mixture. A relative humidity sensor 9 can, for example, measure the resistance or the capacitance of the air and an absolute humidity sensor can, for example, measure the thermal conductivity of the air. Relative humidity sensors 9 and absolute humidity sensors 7 suitable for use in the invention will be known to those skilled in the art. Although the absolute humidity of the exhaled air is required for determining the characteristic of the air that was above the ISB of the subject, the use of a relative humidity sensor 9 is preferred as they tend to be more stable, cheaper and have a faster response time than an absolute humidity sensor. As noted below, the absolute humidity can be derived from measurements of the relative humidity and information on the temperature of the air.

In some embodiments, the air flow sensor 10 can be a sensor that directly measures air flow, but in other embodiments the air flow sensor 10 can be a sensor that measures air pressure (from which air flow can be determined by the control unit 12) or a pair of sensors that are located at different points along the exhalation path in the device 2 a known distance apart and that measure a particular property of the exhaled/inhaled air that varies through the breathing cycle. Suitable properties include temperature and humidity (in which case humidity sensor 8 can be one of the sensors in the air flow sensor 10). The air flow can be determined in the control unit 12 from the time difference between the arrival of a particular part of exhaled air or air being inhaled at each of the two sensors (the particular part having an identifiable value for the property, e.g. a sudden increase in the humidity or temperature at the start of the exhalation). The use of a sensor that measures air pressure is preferred as they consume less power and are cheaper than sensors that directly measure the air flow. The air flow Q can be calculated from the air flow resistance R of the breathing tube 6 (which can be determined from the shape and configuration of the breathing tube 6) and the air pressure measurements P using $$Q=P/R \qquad (1)$$

The volume of the exhaled air (and inhaled air if required) can be determined by integrating the flow (Q) over time (t):

$$V=\int Q(t)dt \qquad (2)$$

between $t_{start}$ and $t_{end}$, which represent the times at which the exhalation (or inhalation) starts and ends respectively.

In some embodiments the device 2 can comprise one or more additional sensors for measuring other properties of the exhaled air and/or air as it is being inhaled by the subject through the device 2. The measurements of these properties can be used to correct or calibrate the characteristic of the air that was above the ISB provided by the device 2. For example, the device 2 can comprise a temperature sensor for measuring the temperature of the air, and the measurement of temperature can be used by the control unit 12 to determine the absolute humidity of the air from a measurement of the relative humidity (this is described in more detail below).

In some embodiments, additional information on the subject is required in order to more accurately determine the characteristic of the air that was above the ISB, and the device 2 can be provided with means to allow this information to be collected or input into the device 2. For example, in some embodiments the weight of the subject, the height of the subject or the body mass index (BMI) of the subject can be used to correct the characteristic of the air that was above the ISB to the shape and/or size of the subject. In this case, the device 2 can allow the weight of the subject, the height of the subject or the BMI to be manually input into the device 2 via a user interface.

In use, the subject breathes through the device 2 and the sensors in the device 2 measure the appropriate properties of the air flowing through the device 2. In some embodiments, the properties can be measured over a number of consecutive or non-consecutive breaths, both during inhalation and exhalation. The measured properties can be averaged over multiple breaths, or the measured properties for a single breath (e.g. the first, the last, or an intermediate breath) can be used in the subsequent analysis. The measurements from the air flow sensor 10 can be used to identify when the subject is inhaling and exhaling (e.g. in the case of the air flow sensor 10 being a pressure sensor inhalation can be indicated by negative pressure and exhalation indicated by positive pressure), and this can be used to identify the parts of the measurements from the humidity sensor 8 relating to inhalation and exhalation.

Figure 3:
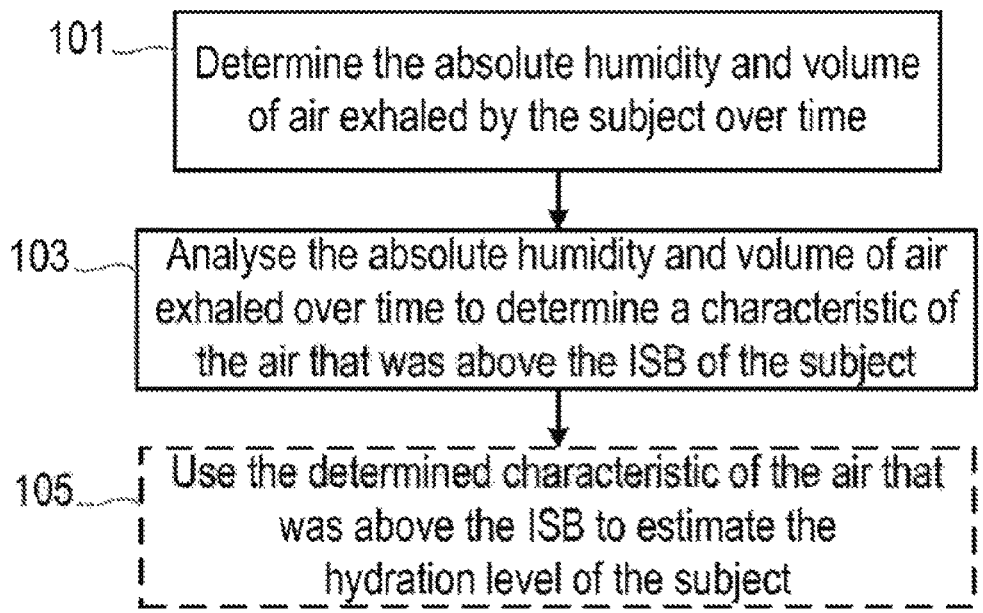
FIG. 3 is a flow chart illustrating a method according to an embodiment of
the invention.

A method of determining the health of a subject according to an embodiment is shown in FIG. 3. In step 101, the device 2 determines the absolute humidity and volume of air exhaled by the subject over time. In particular, the device 2 determines these parameters over at least a first part of an exhalation, or at least a complete exhalation or a number of exhalations. The device 2 determines the value of the absolute humidity and volume of air exhaled at various time points throughout an exhalation so that it is possible to observe changes in the absolute humidity and the volume of exhaled air throughout the exhalation.

In a further embodiment the device 2 further controls the ambient conditions of the air to be inhaled by the subject over time.

As noted above, depending on the sensors 8, 10 provided in the device 2, the device 2 may measure absolute humidity and/or volume of exhaled air directly, or one or both of absolute humidity and volume of exhaled air can be measured indirectly and step 101 can comprise determining the absolute humidity and/or volume of exhaled air from those indirect measurements.

Once the measurements of absolute humidity and volume of exhaled air have been obtained, they are analysed in step 103 to determine a characteristic of the air that was above the ISB of the subject.

As noted above, the ISB of the subject is the point in the respiratory system of the subject where inhaled air reaches body temperature (around 37° C.) and is completely saturated with water (around 44 grams/metre$^3$). The ISB is a point approximately 5 cm below the carina. Above this point in the respiratory tract (i.e. above the ISB), the temperature and humidity decrease during inhalation and increase during exhalation. Below the ISB, i.e. deeper into the lungs, the temperature and humidity are constant. In a subject that is dehydrated, the ISB is lower in the respiratory system (i.e. closer to the lungs) than in a subject that is sufficiently hydrated. The location of the ISB or other measure of the ISB in the subject can be observed or inferred from a characteristic of the air that was above the ISB in the subject following an inhalation. This characteristic is determined from the measurements of the absolute humidity and volume of exhaled air during exhalation.

In one embodiment, as described in more detail below, the volume of air above the ISB in the subject can be determined. This volume is denoted $V_{ISB}$ and corresponds to the volume of air in the airway of the subject that is not yet at body temperature or completely saturated with water. The larger this volume, $V_{ISB}$, the more the subject is dehydrated.

The volume $V_{ISB}$ can be determined by identifying the time at which the absolute humidity reaches a maximum level (e.g. 44 grams/metre$^3$), which is denoted $t_{ISB}$, and then determining the volume of air exhaled by the subject from the start of the exhalation until time $t_{ISB}$. The time $t_{ISB}$ is the time at which the absolute humidity reaches the absolute humidity in the lungs of the subject. In some embodiments below however, $t_{ISB}$ can be the time at which the absolute humidity is at a predetermined amount of the maximum value (the value of the absolute humidity in the lungs of the subject). Thus, in some embodiments the predetermined amount is 100%, but in other embodiments, the predetermined amount can be below 100%, for example 95%. This may be useful where artefacts or noise in the humidity measurements or processing may prevent a 100% value from being measured.

Figure 4:
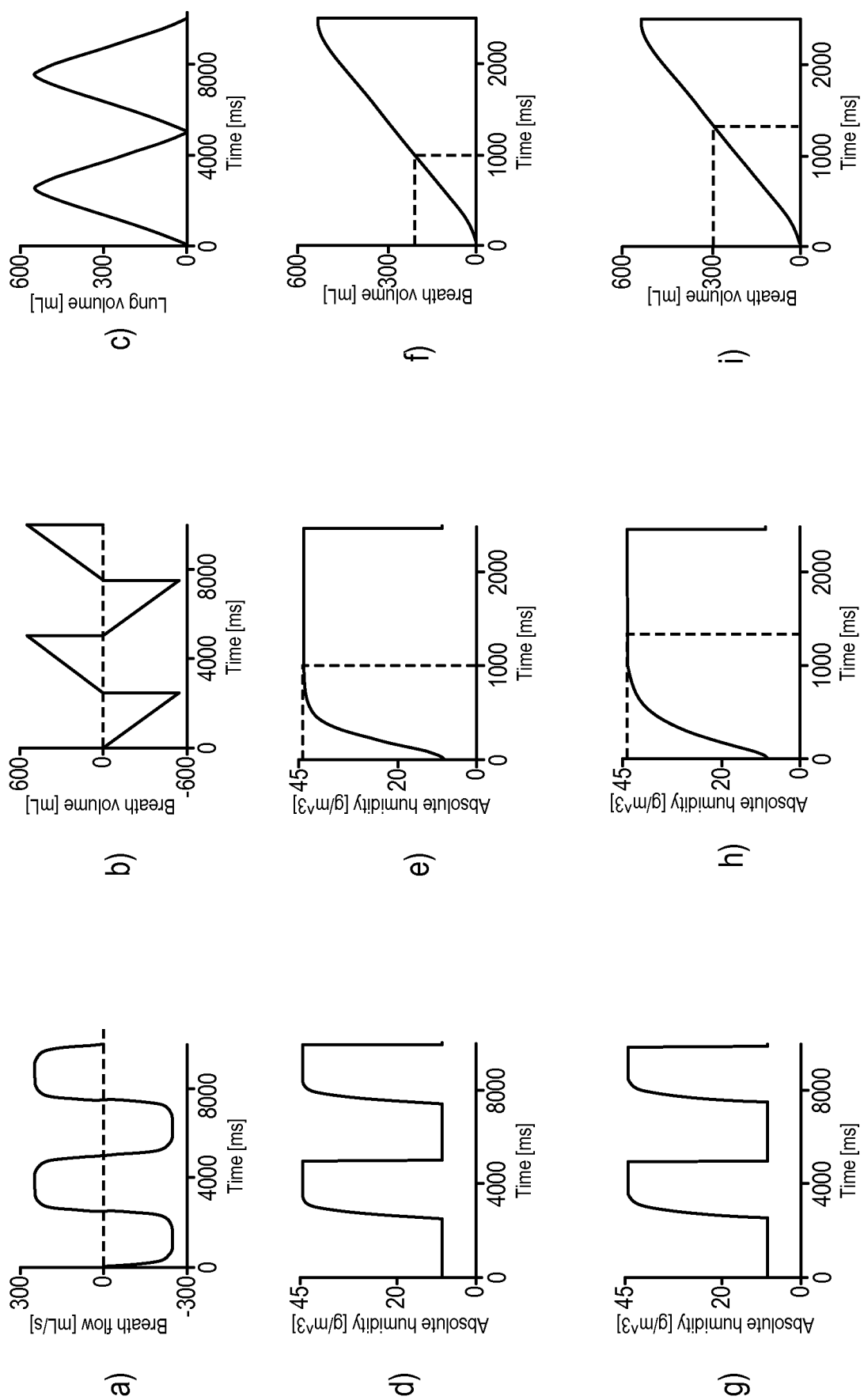
FIG. 4 shows a number of plots labelled a) to i) of absolute humidity and breath volume.

FIG. 4 shows some simulated plots of breath flow, breath volume, lung volume, and absolute humidity for a subject with different ISBs (caused by differing hydration levels). It will be appreciated that FIG. 4 is provided to aid understanding of the invention only, it is not necessary for the device 2 to generate plots from the measurements of absolute humidity and exhaled volume (or breath flow rate in embodiments where the flow rate is measured) in order to determine the characteristic of the air that was above the ISB.

In FIG. 4, plot (a) shows the breath flow during inhalation and exhalation for two cycles of breathing. Inhalation corresponds to negative flow and exhalation corresponds to positive flow. Plot (b) shows the corresponding volume of inhaled and exhaled air over time (which can be derived from plot (a) by integrating the breath flow, Q as shown in equation (2) above over the duration of each inhalation and exhalation). Plot (c) shows the lung volume over time which can easily be derived from the information in plot (b). A typical adult breath contains around 550 mL of air, which is inhaled and exhaled over 2.5 seconds, with a maximum flow of around 250 mL/s.

Plots (d), (e) and (f) relate to a subject that is mildly dehydrated, and plots (g), (h) and (i) relate to the same subject that is now severely dehydrated. Plots (d) and (g) each show the same two breath cycles as in plots (a)-(c), but plots (e), (f), (h) and (i) each show a single exhalation (and it will be noted that t=0 in plots (e), (f), (h) and (i) does not correspond to t=0 in the other plots).

In plots (d) and (g) it can be seen that the absolute humidity of the inhaled air (which can also be measured by the humidity sensor 8) is a bit below 10 g/m$^3$ (corresponding to an air temperature of 20° C. and 50% relative humidity; not shown in FIG. 4) and that the maximum exhaled absolute humidity is around 44 g/m³ (corresponding to a temperature of the air of 37° C and 100% relative humidity; not shown).

Plots (e) and (f) respectively show the absolute humidity and exhaled volume during one exhalation of the subject when they are mildly dehydrated. The time at which the maximum absolute humidity is reached, $t_{ISB}$, can be identified, and in this example $t_{ISB}$ is approximately 1000 ms (the vertical line in plot (e)), which corresponds to a volume, $V_{ISB}$, of 220 mL (shown by the horizontal line in plot (f)). If this $V_{ISB}$ is related to a hydration status as described below with reference to Table 3, a $V_{ISB}$ of 220 mL for a subject that weighs 90 kg indicates dehydration index I, which is mildly dehydrated.

Plots (h) and (i) respectively show the absolute humidity and exhaled volume during one exhalation of the same subject when they are severely dehydrated. The time after which the maximum absolute humidity is reached, $t_{ISB}$, is now approximately 1400 ms (shown by the vertical line in plot (h)), which corresponds to a volume, $V_{ISB}$, of 300 mL (the horizontal line in plot (i)). If this $V_{ISB}$ is related to a hydration status as described below with reference to Table 3, a $V_{ISB}$ of 300 mL for a subject that weighs 90 kg indicates dehydration index III, which is severely dehydrated.

In other embodiments of step 103, alternative measures of the ISB can be derived from analysis of how the absolute humidity changes over time during the exhalation. For example, the characteristic of the air that was above the ISB can be derived from a characteristic of the absolute humidity-time plot, such as the slope, gradient, rate of change, or rising slope at a specific time (less than $t_{ISB}$) or during a specific part of the exhalation, the amplitude of the absolute humidity after a specific time interval from the start of the exhalation (the specific time or specific time interval in either of these alternatives could be a set or fixed time after the start of the exhalation and less than $t_{ISB}$ (for example 1 second from the start of the exhalation), or it could be the time (before $t_{ISB}$) from the start of the exhalation corresponding to the point in the exhalation where the subject has exhaled a predetermined volume of air), the area under the humidity-time plot (i.e. the integral of humidity over a particular time interval, such as that corresponding to a complete exhalation) or area under a specific part of the humidity-time plot (i.e. the integral of humidity over a particular time interval e.g. from the start of the exhalation until time $t_{ISB}$, from the start of the exhalation until a time that is less than $t_{ISB}$, or from a time after the start of the exhalation until $t_{ISB}$ or a time that is less than $t_{ISB}$). A dehydrated subject will have a smaller area under (part of) the absolute humidity-time plot than a more hydrated/less dehydrated subject. A dehydrated subject will have a shallower slope to the absolute humidity-time plot than a more hydrated/less dehydrated subject.

Since the characteristics of the absolute humidity-time plot depend in part on the flow rate at which the subject is breathing (i.e. a higher flow rate should naturally lead to a steeper rise in the absolute humidity which may not therefore be immediately indicative of the ISB or the health of the subject), the characteristic of the absolute-humidity time plot may need to be corrected using the measurements of the exhaled volume (or flow rate if the flow rate was measured by the sensor 10) to determine the characteristic of the air that was above the ISB. In some embodiments, the correction can be performed by dividing the measured characteristic by the corresponding volume or flow rate (i.e. the characteristic is normalised).

The characteristic is preferably measured from the first part of the exhalation, since this part of the exhalation corresponds to air from the subject that is above the ISB.

Figure 5:
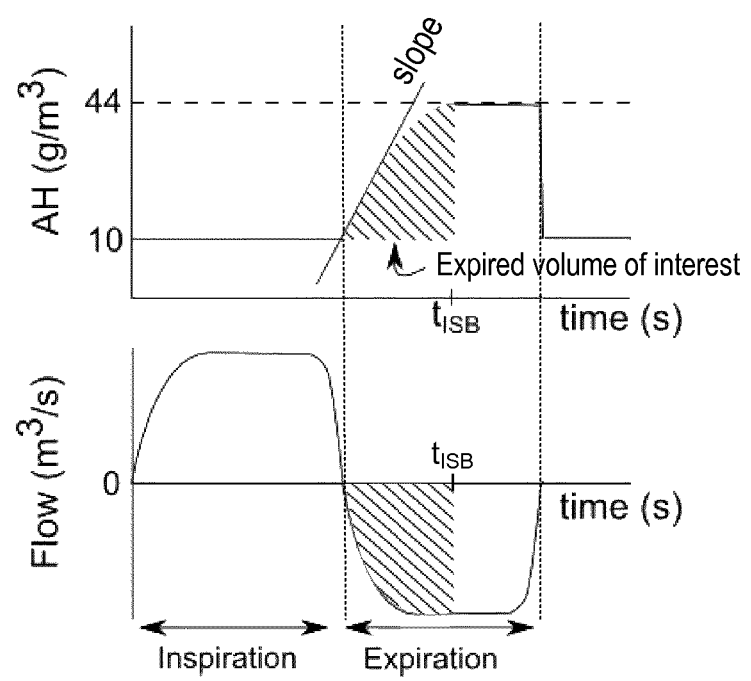
FIG. 5 shows two graphs illustrating how the slope and/or area of the absolute humidity-time plot can be determined.

The graphs in FIG. 5 illustrate the calculation of the slope of and area under an exemplary absolute humidity-time curve.

In some embodiments, which are described in more detail below, in determining the characteristic of the air that was above the ISB, step 103 can comprise correcting or compensating the determined characteristic of the air that was above the ISB for the temperature and/or humidity of the air inhaled by the subject.

In some embodiments, multiple ones of the characteristics described above can be determined for a particular subject, and the characteristics analysed together in order to determine the health of the subject.

Although the characteristic of the air that was above the ISB can indicate the health of the subject by itself, in some embodiments the method can further comprise using the determined characteristic of the air that was above the ISB to estimate the hydration level of the subject (step 105). The value of the characteristic of the air that was above the ISB can be related to a hydration level of the subject through a look-up table or chart (for example as shown in Table 3 below) that links specific values or ranges of values of the characteristic of the air that was above the ISB to a specific hydration level (e.g. hydrated, mildly dehydrated, moderately dehydrated, severely dehydrated, etc.).

In preferred embodiments, step 105 can also take into account characteristics of the subject, such as weight, height or BMI when translating the characteristic of the air that was above the ISB into an indication of the hydration of the subject. This correction for the size and/or shape of the subject (and specifically weight) is illustrated in Table 3 below.

In some embodiments the device 2 can output the value of the characteristic of the air that was above the ISB to the subject or a clinician and they can manually compare the value to a look-up table or chart to determine the hydration status. In other embodiments, the look-up table or chart can be 'built-in' to the device 2 so that the device 2 determines the hydration status directly from the characteristic of the air that was above the ISB in step 105 (and any measure of the subject's weight, height or BMI that is input to the device 2).

Figure 6:
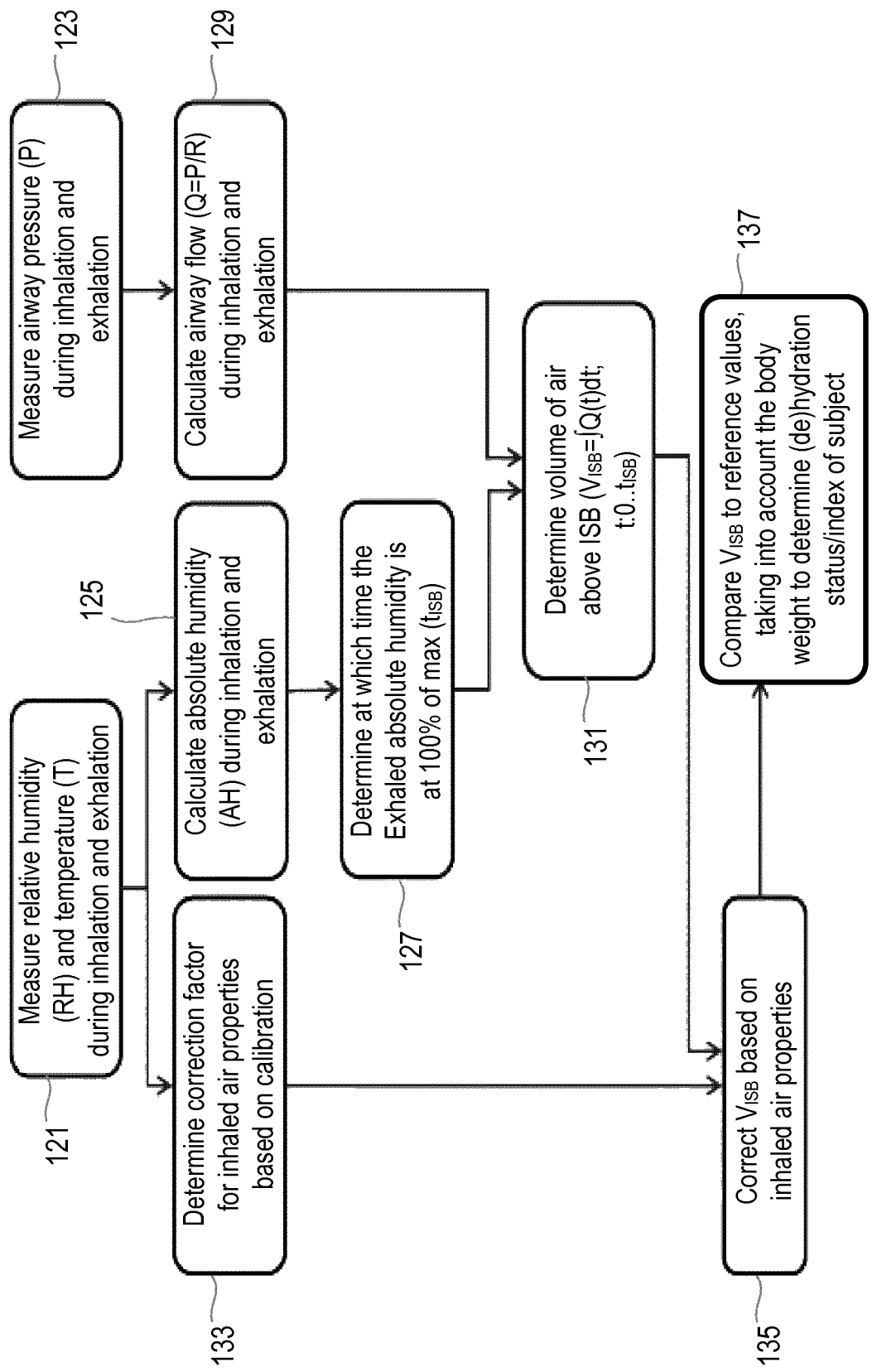
FIG. 6 is a flow chart illustrating a method according to a preferred embodiment of the invention.

The flow chart in FIG. 6 illustrates a preferred embodiment of the invention in which the volume of air above the ISB, $V_{ISB}$, in the subject is determined and the $V_{ISB}$ related to the hydration state of the subject. It will be appreciated that the various features and steps shown in FIG. 6 can be applied individually or in any reasonable combination to the general method shown in FIG. 3.

In this illustrated embodiment, the device 2 comprises a relative humidity sensor 8, a temperature sensor for measuring the temperature of the air as it passes through the device 2 and an air pressure sensor 10 for measuring the pressure of the air in the device 2.

In the first steps, step 121 and 123, the sensors 8, 10 and the temperature sensor measure the relevant properties of the air as the subject inhales and exhales through the device 2. In a further embodiment the device controls the ambient conditions of the air that the subject inhales.

The measurements of the relative humidity (RH) and temperature (T) are used to calculate the absolute humidity (AH) of the air during inhalation and exhalation. In one embodiment, the absolute humidity can be calculated from the relative humidity and temperature measurements, via the water vapour pressure ($p_w$) and the water vapour saturation pressure ($p_{ws}$) as follows:

$$p_{ws}(T) = A \cdot 10^{\left(\frac{m \cdot T_n}{T+T_n}\right)} \quad (3)$$

$$p_w = p_{ws} \cdot RH/100 \quad (4)$$

$$AH = C \cdot p_w/T \quad (5)$$

where T is measured in ° C. and $T_n$ is measured in Kelvin. Table 1 below indicates the values for the constants shown in equations (3)-(5) and apply to water in a temperature range of −20 . . . +50° C.

TABLE 1

| Constant | Value | |
|---|---|---|
| A | 6.116441 | |
| m | 7.591386 | |
| $T_n$ | 240.7263 | Triple point temperature [K] |
| C | 2.16679 | [gK/J] |

Next, in step 127, it is determined from the measurements of absolute humidity during the exhalation (with the exhalation parts being identified from the measurements of air pressure from sensor 10) the time at which the absolute humidity of the exhaled air is at a predetermined amount of the maximum value. Preferably this predetermined amount is 100% of the maximum value (i.e. the predetermined amount is the maximum value), but in other embodiments, the predetermined amount can be less than 100% (for example to allow for the possibility that due to noise or artefacts in the humidity measurements or processing a 100% value may not be measured). For example, the predetermined amount can be 95% of the maximum value. The time determined in step 127 at which the absolute humidity of the exhaled air is at the predetermined amount of the maximum value (e.g. 100% or a specified percentage below 100%) is denoted in the following as $t_{ISB}$ (even though it will be appreciated that at a predetermined amount below 100% $t_{ISB}$ does not fully indicate the ISB).

In step 129, the measurements of air pressure from the air pressure sensor 10 are processed to determine the flow rate during exhalation and inhalation.

The air flow resistance (R) of the breathing tube 6 will be known, so the air pressure (P) measurements can, after calibration, easily be converted to air flow (Q) using equation (1) above.

Next, in step 131, the $V_{ISB}$ is determined from the exhalation flow rates calculated in step 129 and $T_{ISB}$ that was determined in step 127. In particular, $V_{ISB}$ is calculated by integrating the exhalation flow rate Q from the start of the exhalation until time $t_{ISB}$:

$$V_{ISB} = \int Q(t)dt; \ t=0 \ldots t_{ISB} \quad (6)$$

To obtain a reliable measure of the $V_{ISB}$, it is necessary to correct the $V_{ISB}$ for the ambient conditions around the device 2, and in particular for the properties of the inhaled air. Thus, in step 133, a correction factor for $V_{ISB}$ is determined based on the properties of the inhaled air, such as temperature and relative humidity (or alternatively just the absolute humidity if that is measured directly). The temperature and humidity of the inhaled air affect the water exchange efficiency within the subject. In this embodiment, the correction factor for $V_{ISB}$ is determined using a calibration table or function. An exemplary calibration table is shown as Table 2 below. It will be appreciated that this table only shows a small set of possible values for temperature (T) and relative humidity (RH).

TABLE 2

| Temperature, T [° C.] | Relative Humidity, RH [%] | Correction factor, CF |
|---|---|---|
| 10 | 50 | 0.8 |
| 15 | 50 | 0.9 |
| 20 | 50 | 1.0 |
| 25 | 50 | 1.1 |
| 30 | 50 | 1.2 |
| 20 | 10 | 0.6 |
| 20 | 30 | 0.8 |
| 20 | 50 | 1.0 |
| 20 | 70 | 1.2 |
| 20 | 90 | 1.4 |

In this example, the calibration function used to determine the correction factor CF is given by $$CF = 1 + 0.02*(T-20) + 0.01*(H-50) \quad (7)$$

and it will be appreciated that this calibration function can be used instead of using a look-up table. Those skilled in the art will appreciate that other equations for determining a correction factor can be used.

After step 133, the correction factor is used to correct the $V_{ISB}$ determined in step 131 for the ambient conditions (step 135). In particular the $V_{ISB}$ is multiplied by the correction factor CF to determine a corrected $V_{ISB}$, which is denoted $V_{ISB\_CORRECTED}$.

Next, in step 137, $V_{ISB\_CORRECTED}$ is compared to reference values, which take into account physical characteristics of the subject, such as their weight, in order to determine the hydration status of the subject. Exemplary reference values are shown in Table 3 below.

TABLE 3

| Weight [kg] | Normal $V_{ISB}$ range [mL] | Dehydration index I | II | III |
|---|---|---|---|---|
| 40 | <92 | 92-101 | 101-110 | >110 |
| 50 | <116 | 116-127 | 127-138 | >138 |
| 60 | <139 | 139-152 | 152-165 | >165 |
| 70 | <162 | 162-177 | 177-193 | >193 |
| 80 | <185 | 185-202 | 202-220 | >220 |
| 90 | <208 | 208-228 | 228-248 | >248 |
| 100 | <231 | 231-253 | 253-275 | >275 |
| 110 | <254 | 254-278 | 278-303 | >303 |
| 120 | <277 | 277-304 | 304-330 | >330 |

It will be appreciated by those skilled in the art that not all of the steps in FIG. 6 have to be performed in the order recited above.

Figure 7:
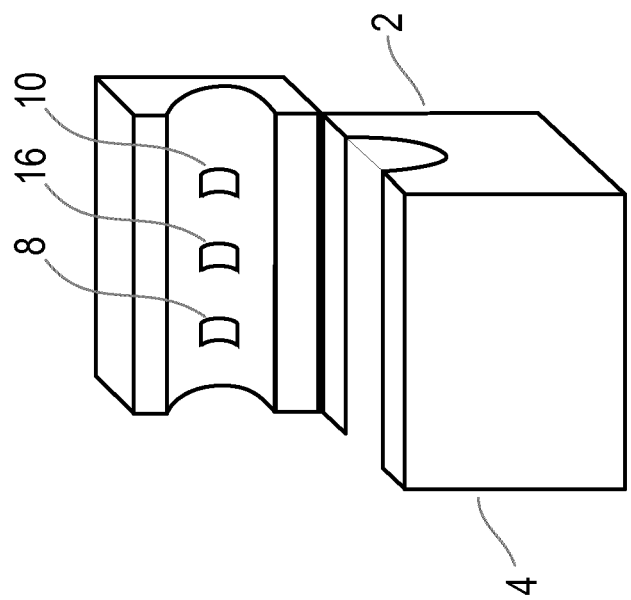
FIG. 7 is a diagram illustrating a device according to an embodiment of the invention that has a removable breathing tube.
Figure 7:
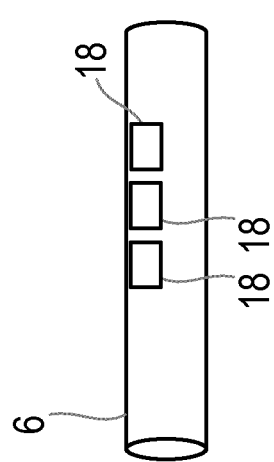

FIG. 7 illustrates an exemplary embodiment of the device 2 shown in FIG. 1. In this exemplary embodiment, the breathing tube 6 is a disposable component of the device 2, with the main housing 4 being configured to allow the breathing tube 6 to be removed and replaced. The sensors 8, 10 (and temperature sensor 16 in this embodiment) are part of the main housing 4 and the breathing tube 6 is provided with a number of holes 18 corresponding to the sensors 8, 10, 16 to enable the sensors to measure the properties of the air passing through the tube 6 when the tube 6 is installed in the main housing 4. Such a device 2 is simple and low-cost (since temperature, relative humidity and air pressure sensors are relatively cheap and reusable), provides a diagnosis of dehydration, and is especially suited to primary care and non-professional use (non-medical caregivers, family, etc.). In this illustrated embodiment, the sensors 8, 10, 16 are arranged on the upper side of the tube 6 to reduce the chance of contamination of the sensors by, for example, saliva excreted with the exhaled breath.

In some embodiments, the method and device 2 can be implemented into a mechanical ventilator system 11 that provides ventilation of home and hospital patients, to provide 'humidity on demand' (i.e. to adjust the humidity of ventilator air according to the airway conditions of the subject as measured by the device 2). The method is easiest to apply on subjects that have been tracheotomised, since they form a closed circuit with the ventilator. They coincidentally also benefit most from adequate humidification because humidifying tissue in the upper airways is bypassed by the tracheotomy. For subjects ventilated with a mask, a level of leak (i.e. an amount of air escaping the circuit on the mask interface) is expected. This might influence the characteristic of the air that was above the ISB obtained by the method, but it could be compensated with the estimated leak rate, as calculated by the ventilator.

For incorporation into a closed-loop mechanical ventilation system (11 in FIG. 2), the humidity sensor 8 should be able to measure humidity changes at a speed high enough to offer sufficient resolution during the inhalation and exhalation time. Such resolution requires sub second sampling. Many absolute humidity sensors commonly used in commercial appliances have a response time in the range of seconds so the use of relative humidity sensors is preferred.

When used in a mechanical ventilation system, the air flow and air volume data monitored by the ventilator can be used in the method described above, which means that a separate air pressure or air flow sensor is not required.

In some embodiments, instead of measuring the temperature and humidity of the inhaled air and using them to correct the characteristic of the air that was above the ISB for the ambient conditions as in steps 133 and 135, the ambient conditions can be controlled by an air acclimatiser or other suitable apparatus. The target temperature for the inhaled air should be well below body temperature, preferably close to room temperature (e.g. around 20° C.). The relative humidity at the target temperature should be around or below 50%. This way a known humidity deficit is created, a temperature difference of 17° C. and humidity difference of 50%. This simplifies the calibration of the device 2. Furthermore the device 2 can be used in all circumstances, regardless of the outside temperature and humidity.

There is therefore provided a method and device for determining the health of a subject that determines a characteristic of the air that was above the ISB of the subject from an analysis of exhaled breath.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of determining the health of a subject using a handheld device, the method comprising:
   receiving, at a breathing tube of the handheld device, air exhaled through a mouth or nose of the subject over time during exhalation;
   determining, using a sensor integral with the handheld device, an absolute humidity of air exhaled by the subject over time during exhalation;
   determining, using a controller integral with or in communication with the handheld device, a time $t_{ISB}$ at which the absolute humidity reaches a maximum level;
   analysing the determined absolute humidity of air exhaled by the subject prior to the time $t_{ISB}$ to determine a characteristic of air in the respiratory system of the subject above the isothermic saturation boundary (ISB); and
   estimating, using the determined characteristic of the air that was in the respiratory system of the subject above the ISB, a hydration level of the subject.

2. A method as claimed in claim 1, wherein the step of using the characteristic of the air that was in the respiratory system of the subject above the ISB to estimate the hydration level comprises correcting the characteristic of the air that was in the respiratory system of the subject above the ISB for the shape and/or size of the subject.

3. A method as claimed in claim 1, the method further comprising the step of:
   correcting the characteristic of the air that was in the respiratory system of the subject above the ISB for the ambient conditions of the air inhaled by the subject.

4. A method as claimed in claim 1, wherein the characteristic of the air that was in the respiratory system of the subject above the ISB is any one or more of:
   (i) the volume of air in the respiratory system of the subject above the ISB;
   (ii) the area under a plot of the absolute humidity against time;
   (iii) the area under part of a plot of the absolute humidity against time;
   (iv) the amplitude of the absolute humidity after a specific time interval from the start of the exhalation; and
   (v) the slope, gradient, rate of change or rising slope of the absolute humidity at a specific time or over part of the exhalation by the subject.

5. A non-transitory computer readable medium comprising computer readable code, the computer readable code being configured such that, on execution by a suitable computer, processor or control unit of a handheld device, the computer, processor or control unit is caused to:
   receive, at a breathing tube of the handheld device, air exhaled through a mouth or nose of a subject over time during exhalation;
   determine, using a sensor integral with the handheld device, an absolute humidity of air exhaled by the subject over time during exhalation;
   determine a time $t_{ISB}$ at which the absolute humidity reaches a maximum level;

analyze the determined absolute humidity of air exhaled by the subject prior to the time $t_{ISB}$ to determine a characteristic of air in the respiratory system of the subject above the isothermic saturation boundary, ISB, before exhalation; and estimate, using the determined characteristic of the air that was in the respiratory system of the subject above the ISB, a hydration level of the subject.

6. A device for determining the health of a subject, the device comprising:

a breathing tube to receive air exhaled through a mouth or nose of the subject over time during exhalation;

a sensor to provide a signal indicative of an absolute humidity of the air exhaled by the subject over time during exhalation;

a control unit configured to determine the absolute humidity based on the sensor signal; determine a time $t_{ISB}$ at which the absolute humidity approximately reaches a maximum level;

analyse the determined absolute humidity of air exhaled by the subject prior to time $t_{ISB}$ to determine a characteristic of air in the respiratory system of the subject above the isothermic saturation boundary, ISB, before exhalation; and estimate, using the determined characteristic of the air that was in the respiratory system of the subject above the ISB, a hydration level of the subject.

7. A device as claimed in claim 6 wherein the control unit is further configured to use the characteristic of the air that was in the respiratory system of the subject above the ISB to estimate the hydration level of the subject by comparing the characteristics of the air that was in the respiratory system of the subject above the ISB to a set of reference values.

8. A device as claimed in claim 6, wherein the sensor comprises an absolute humidity sensor for measuring the absolute humidity of the air exhaled by the subject.

9. A device as claimed in claim 6, wherein the sensor comprises a relative humidity sensor and a temperature sensor for measuring the relative humidity and temperature of the air exhaled by the subject respectively, and wherein the control unit is configured to determine the absolute humidity of air exhaled by the subject over time from the measured relative humidity and temperature.

10. A device as claimed in claim 6, wherein the device further comprises an air flow sensor for measuring the flow of air exhaled by the subject, and wherein the control unit is configured to determine a volume of air exhaled by the subject from the measured flow rate.

11. A device as claimed in claim 6, wherein the device further comprises an air pressure sensor for measuring the air pressure as air is exhaled by the subject, and the control unit is configured to determine a volume of air exhaled by the subject from the measured air pressure.

12. A device as claimed in claim 6, wherein the characteristic of the air that was in the respiratory system of the subject above the ISB is any one or more of (i) the volume of air in the respiratory system of the subject above the ISB; (ii) the area under a plot of the absolute humidity against time; (iii) the area under part of a plot of the absolute humidity against time; (iv) the amplitude of the absolute humidity after a specific time interval from the start of the exhalation; and (v) the slope, gradient, rate of change or rising slope of the absolute humidity at a specific time or over part of the exhalation by the subject.

13. A device as claimed in claim 6, wherein the breathing tube comprises a mouthpiece, a nasal cannula, a nasal mask, a nasal oral mask, a full face mask, or a total face mask, the breathing tube being further connectable to a ventilation system for providing ventilation of the subject.

14. A ventilation system for providing ventilation of a subject, the ventilation system comprising the device as claimed in claim 6, the ventilation system further being configured to adjust the humidity of ventilator air provided by the ventilation system to the subject.

\* \* \* \* \*